United States Patent
Luloh et al.

(10) Patent No.: US 7,060,028 B2
(45) Date of Patent: Jun. 13, 2006

(54) ENDOILLUMINATOR

(75) Inventors: K. Peter Luloh, Stuart, FL (US);
James Dodsworth, Jensen Beach, FL (US); Michael Annen, Sanford, FL (US)

(73) Assignee: Insight Instruments, Inc., Stuart, FL (US)

( * ) Notice: Subject to any disclaimer, the term of this patent is extended or adjusted under 35 U.S.C. 154(b) by 249 days.

(21) Appl. No.: 10/741,462

(22) Filed: Dec. 19, 2003

(65) Prior Publication Data

US 2004/0249424 A1  Dec. 9, 2004

Related U.S. Application Data

(60) Provisional application No. 60/476,523, filed on Jun. 6, 2003.

(51) Int. Cl.
*A61B 1/06* (2006.01)

(52) U.S. Cl. .............................. 600/182; 606/4; 606/15

(58) Field of Classification Search ................ 600/121, 600/160, 178, 180, 182; 606/1, 2, 4–6, 13–16
See application file for complete search history.

(56) References Cited

U.S. PATENT DOCUMENTS

| | | |
|---|---|---|
| 5,078,712 A | 1/1992 | Easley et al. |
| 5,203,353 A | 4/1993 | Easley et al. |
| 5,354,302 A * | 10/1994 | Ko .............................. 606/104 |
| 5,425,730 A | 6/1995 | Luloh |
| 5,651,783 A | 7/1997 | Reynard |
| 6,428,553 B1 | 8/2002 | Trese |
| 6,585,727 B1 | 7/2003 | Cashman et al. |

* cited by examiner

*Primary Examiner*—Beverly M. Flanagan
(74) *Attorney, Agent, or Firm*—James H. Beusse; Beusse Wolter Sanks Mora & Maire, P.A.

(57) ABSTRACT

A fiber optic endoilluminator surgical instrument for projecting illuminating light into an interior of an eyeball includes a finger grip member and an elongated passageway through the finger grip member. A hollow rigid needle, adapted to penetrate into the interior of the eyeball, slidably extends from one end of the grip member. An optical fiber extends through the needle and the grip member, and a lever is connected to the needle for allowing the needle to be moved to and fro with respect to the grip member for varying the amount of optical fiber exposed at an illumination end portion of the fiber. By covering the illumination end portion with the needle, a spot of illumination is provided for viewing a comparatively smaller portion of the interior of the eyeball. By uncovering the illumination end portion, a flood of illumination is provided for viewing a comparatively larger portion of the interior of the eyeball.

2 Claims, 1 Drawing Sheet

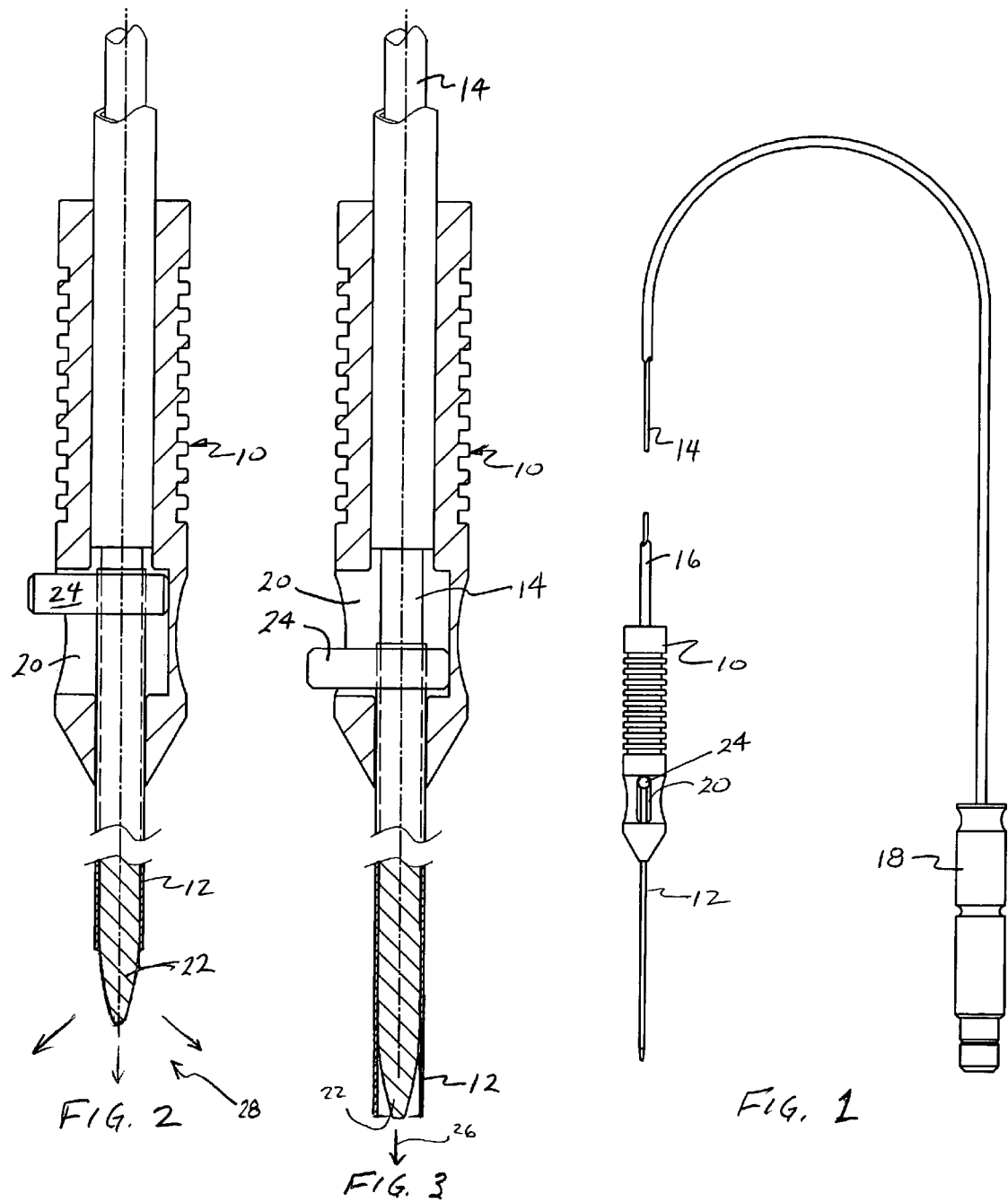

ENDOILLUMINATOR

SPECIFIC DATA RELATED TO THE INVENTION

This application claims the benefit of U.S. Provisional Patent Application Ser. No. 60/476,523, filed on Jun. 6, 2003.

FIELD OF THE INVENTION

The present invention relates to an endoscopic surgical instrument and, more particularly, an endoscopic illuminator useful in eye surgery for illuminating an interior area of an eyeball of a patient to be operated upon.

BACKGROUND OF THE INVENTION

Fiber optic light sources are commonly used in ophthalmic surgery to illuminate an interior area of the eyeball for inspection, diagnosis, and surgery. However, conventional fiber optic illuminators are typically configured to emit a relatively narrow beam of light from an end of the fiber. As a result, such illuminators may only provide spot illumination of a relatively small portion of the interior of the eyeball. While such spot illumination is suitable for viewing a relatively small area, it is often desirable to illuminate a larger area. For example, when performing eye surgery or invasive examination of the interior of the eye, it is typically necessary to illuminate a large area for orientation and then be able to concentrate the illumination on a smaller portion of the large area to perform the required surgery or examination.

SUMMARY OF THE INVENTOIN

A method of illuminating an interior of an eyeball with an optical fiber positioned within the eyeball is described herein as including disposing a tubular sheath around the optical fiber proximate an illumination end portion. The method also includes covering the illumination end portion with the sheath to provide a spot of illumination on a comparatively smaller portion of the interior of the eyeball. The method further includes uncovering the illumination end portion to provide a flood of illumination on a comparatively larger portion of the interior of the eyeball.

A fiber optic endoilluminator surgical instrument for projecting illuminating light into an interior of an eyeball is described herein as including a finger grip member having a first end and a second end and an elongated passageway through the finger grip member from the first end to the second end. The instrument also includes a hollow rigid needle adapted to penetrate into the interior of the eyeball, the needle slidably extending from the first end of the grip member and an optical fiber extending through the needle and the grip member, the optical fiber having a sheath and being connectable to a light source. The instrument further includes a lever connected to the needle for allowing the needle to be moved to and fro with respect to the grip member for varying the amount of optical fiber exposed at a distal end of the needle.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 illustrates an overall view of the endoilluminator of the present invention.

FIG. 2 is an expanded, cross-sectional view of a finger grip member of the endoilluminator with a needle extended for covering an optical fiber.

FIG. 3 is an expanded, cross-sectional view of the finger grip member of the endoilluminator with the needle retracted for uncovering an optical fiber.

DETAILED DESCRIPTION OF THE INVENTION

The present invention relates to a surgical instrument for use in penetrating and working in the vitreous humor of an eye and comprises a finger grip member having a slidable tubular sheath, such as a rigid, hollow needle, extending from one end of the finger grip member with a single continuous optical fiber extending from a distal end of the needle, through the needle, the finger grip and exiting from an opposite end of the finger grip. The optical fiber exiting from the opposite end of the finger grip is covered with an opaque sheath and terminates in a connector that enables the optical fiber to be coupled to a light source. The rigid needle at the one end of the finger grip member is preferably formed of stainless steel or other rigid structural material and is adapted to be movable on the optical fiber so that different lengths of an illumination end portion of the optical fiber can be exposed at the distal end of the needle. Such movement of the needle on the optical fiber allows light projecting from the end of the optical fiber to be concentrated in the narrow beam or to be dispersed over a broader area. For example, the illumination end portion of the optical fiber may be covered with the needle to provide a spot of illumination on a comparatively smaller portion of the interior of the eyeball, while uncovering the illumination end portion of the optical fiber may provide a flood of illumination on a comparatively larger portion of the interior of the eyeball. Advantageously, a beamwidth of the light projecting from the end portion may be adjusted without requiring changing the position of the fiber.

FIG. 1 illustrates an overall view of the endoilluminator of the present invention. The endoilluminator includes a hand or finger grip member 10, which may be formed of plastic or other material capable of being sterilized. Extending from one end of the finger grip member 10 is a hollow, rigid needle 12 which functions as a support and light sheath around an optical fiber 14 extending through the needle 12. The optical fiber 14 passes through the finger grip member 10 and outwardly from the finger grip member at an end opposite the needle 12, terminating in a connector 18 adapted for connection to a conventional light source (not shown). The optical fiber 14 is covered with a fixed sheath 16 that prevents light from escaping laterally from the optical fiber between the light source and grip member 10.

Considering FIGS. 1, 2 and 3 together, it can be seen that the needle or sheath 12 is adapted to be movable over a finite distance defined by the length of a slot 20 formed in the finger grip member 10. The position of the needle/sheath covering the end 22 of the optical fiber is determined by movement in the slot 20 of a lever 24 attached to the needle 12. In FIG. 2, the lever 24 is shown moved to the rearward portion of the slot, thereby exposing a larger area of the end 22 of the optical fiber. When the lever 24 is moved forward in the slot 20 as shown in FIG. 3, the needle extends forward over the end 22 of the optical fiber, thereby causing light exiting the optical fiber to be concentrated in a narrow beam 26. Clearly, with the needle withdrawn as shown in FIG. 2, the light will exit the optical fiber 14 over a broader area 28 and therefore provide a wider area of illumination within the eye. In one form, the end 22 of the optical fiber may be shaped, such as tapered, to produce a desired illumination pattern.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A fiber optic endoilluminator surgical instrument for illuminating an interior of an eyeball comprising:

a finger grip member having a first end and a second end;

an elongated passageway through the finger grip member from the first end to the second end;

a hollow rigid needle adapted to penetrate into the interior of the eyeball, the needle slidably extending from the first end of the grip member;

an optical fiber extending through the needle and the grip member, the optical fiber having a sheath and being connectable to a light source; and, a lever connected to the needle for allowing the needle to be moved to and fro with respect to the grip member for varying the amount of optical fiber exposed at a distal end of the needle.

2. The surgical instrument of claim 1 and including a slot formed in the grip member and penetrating into the elongated passageway, the needle lever extending outwardly through the slot.

* * * * *